United States Patent [19]

Ohyama et al.

[11] 4,447,259
[45] May 8, 1984

[54] 2-(SUBSTITUTED PHENOXY)PROPIONIC ACID DERIVATIVES AND THEIR USES FOR HERBICIDAL PURPOSES

[75] Inventors: Hiroshi Ohyama, Chigasaki; Sanae Takada, Atsugi; Ken Morita, Hiratsuka; Saburo Yamamura, Fujisawa, all of Japan

[73] Assignee: Hokko Chemical Industry Co., Ltd., Nihonbashi, Japan

[21] Appl. No.: 447,892

[22] Filed: Dec. 8, 1982

[30] Foreign Application Priority Data

Dec. 18, 1981 [JP] Japan .............................. 56-203416
Sep. 21, 1982 [JP] Japan .............................. 57-163194
Sep. 24, 1982 [JP] Japan .............................. 57-164967

[51] Int. Cl.³ .................... A01N 43/40; C07D 413/02
[52] U.S. Cl. ............................................. 71/94; 71/88; 546/275; 548/240
[58] Field of Search ................... 548/240; 546/275; 71/88, 94

[56] References Cited

U.S. PATENT DOCUMENTS 4,133,675 1/1979 Schurter et al. .................... 546/275
4,213,774 7/1980 Schurter et al. .................... 546/275
4,332,960 6/1982 Trösken et al. ..................... 71/108
4,332,961 6/1982 Takahashi et al. .................. 71/108

Primary Examiner—Jane T. Fan
Attorney, Agent, or Firm—Larson and Taylor

[57] ABSTRACT

New 2-(substituted-phenoxy)propionic acid derivatives are provided, which have the structure of the general formula:

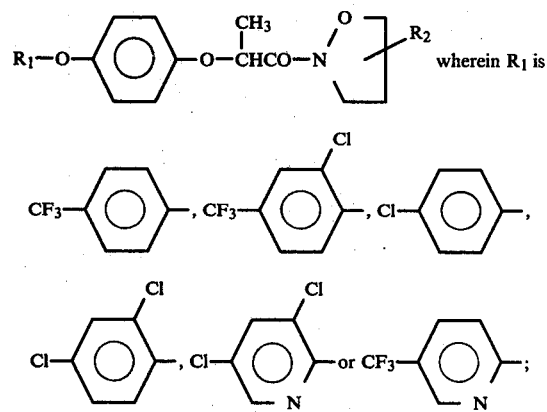

wherein $R_1$ is and $R_2$ is a hydrogen atom or a lower alkyl group. They have a high herbicidal activity to weeds, particularly graminaceous weeds, while they have little or no phytotoxicity to broad leaved crop plants and are therefore useful as selective herbicide.

14 Claims, No Drawings

2-(SUBSTITUTED PHENOXY)PROPIONIC ACID DERIVATIVES AND THEIR USES FOR HERBICIDAL PURPOSES

TECHNICAL FIELD OF THE INVENTION

This invention relates to 2-(substituted phenoxy) propionic acid derivatives as new chemical compounds and their uses for herbicidal purposes.

BACKGROUND OF THE INVENTION

Numerous acid amides derived from aliphatic and aromatic amines have hitherto been synthesized and tested on their herbicidal activity, but they include little or no acid amide derived from isoxazolidine which is a unique heterocyclic amine.

A class of herbicidally active compounds, 2-[4-(4-trifluoromethyl)phenoxy]phenoxypropionic acid and its salts, esters, amides and other derivatives, is disclosed in Japanese patent application unexamined prepublication KOKAI Sho 52-83618, which are represented by the formula:

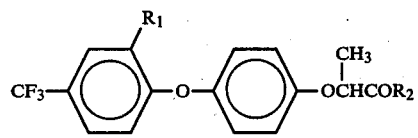

wherein $R_1$ is a hydrogen atom or a halogen atom; $R_2$ is a hydroxy, $(C_{1-4})$alkoxy, cyclohexyloxy, phenyloxy, phenylthio, hydrazino, amino, $(C_{1-4})$alkylamino, di$(C_{1-4})$alkylamino, phenylamino optionally substituted by a halogen or trifluoromethyl on the phenyl nucleus or —Okat group where Kat is a cation of an inorganic or organic base. These compounds have an asymmetric carbon atom adjacent to the carbonyl group, so that they have a pair of optical antiposes, i.e. d- and l-isomers. The d-isomer of these compounds is known to have a high herbicidal activity as disclosed in Japanese patent application KOKAI Sho 54-112828.

It is also known as disclosed in Japanese Patent Publication No. 8727/79 that 2-(substituted phenoxy or substituted phenylthio)aliphatic acids and their salts, esters, amides and other derivatives have a herbicidal activity, which are represented by the formula:

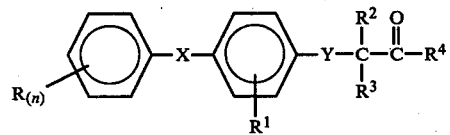

wherein R which may be the same with each other or different from each other is selected from the group consisting of a halogen atom, alkyl having 1 to 4 carbon atoms, alkoxy and alkylthio both having 1 to 4 carbon atoms; $R^1$ is selected from the group consisting of a hydrogen atom, a halogen atom and an alkyl having 1 to 4 carbon atoms; X and Y each is an oxygen atom; n is an integer of 1 to 3; $R^2$ is a halogen atom, an alkyl having 1 to 10 carbon atoms or an alkoxyalkyl containing 2 to 6 carbon atoms; $R_3$ is a hydrogen atom; and $R^4$ is a hydroxy, alkoxy having 1 to 10 carbon atoms, trichloroethyloxy, alkylthio having 1 to 6 carbon atoms, alkenyloxy having 2 to 4 carbon atoms, cyclohexyloxy, methylcyclohexyloxy, phenoxy substituted by one or two halogen atoms, phenylthio optionally substituted by one or two halogen atoms, alkylamino having 1 to 4 carbon atoms, dialkylamino having 1 to 4 carbon atoms in each alkyl group, di-substituted amino having the formula:

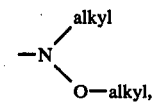

phenylamino substituted by a halogen, —CF$_3$, —OCF$_2$CF$_2$H or —COOCH$_3$ or —O—Kat group where Kat is a cation of an inorganic or organic base. These compounds have an asymmetric carbon atom adjacent to the carbonyl group, so that they have a pair of optial antiposes, i.e. d- and l-isomers. The d-isomer of these compounds is known to have a high herbicidal activity as described in Japanese patent application KOKAI Sho 54-112828.

Japanese patent application KOKAI Sho 52-125626 discloses another class of herbicidally active compounds, 2-[4-(3,5-dichloro-2-pyridyloxy)phenoxy]propionic acid amide derivatives which are represented by the formula:

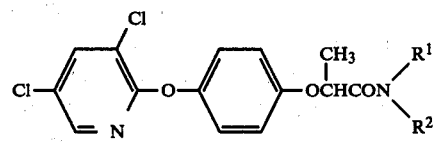

wherein $R^1$ is a hydroxyalkyl, lower alkoxy, lower alkenyloxy, acyl, amino, aralkyl, chloro-substituted aralkyl, —R$^3$COOR$^4$ where R$^3$ is a lower alkylene and R$^4$ is a hydrogen, lower alkyl or salt-forming atom or group, or

where $R^5$ and $R^6$ each are a hydrogen, lower alkyl or lower alkoxy; and $R^2$ is a hydrogen, lower alkyl, lower alkoxy, hydroxyalkyl, phenyl or chloro-substituted phenyl; or

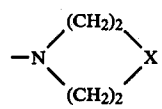

may form a cyclic group

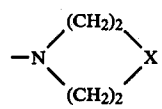

where X is a methylene group or oxygen atom. These compounds have an asymmetric carbon atom adjacent to the carbonyl group, so that they have a pair of optical antipodes, i.e. d- and l-isomers. The d-isomer of these compounds has a high herbicidal activity as described in Japanese patent application KOKAI Sho 54-112828.

Japanese patent application KOKAI Sho 54-122728 discloses a different class of herbicidally active compounds, 4-(5-fluoromethyl-2-pyridyloxy)phenoxyalkane carboxylic acids and their derivatives of the formula:

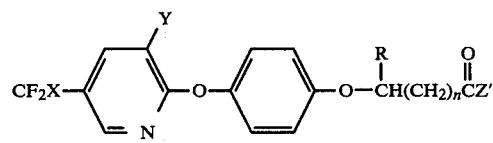

wherein X is a chlorine or fluorine atom; Y is a hydrogen or chlorine atom; R is a hydrogen atom, methyl or ethyl; n is 0 or 2; and Z' is a hydroxyl, lower alkoxy optionally substituted by a halogen atom, lower alkoxyalkoxy, lower alkenyloxy, lower alkynyloxy, cycloalkoxy optionally substituted by a lower alkyl, lower alkoxycarbonylalkoxy, phenoxy optionally substituted by a halogen atom or by lower alkyl, benzyloxy, glycidyloxy, lower alkylthio, lower alkenylthio, phenylthio optionally substituted by a halogen atom or by lower alkyl, amino, lower alkylamino, lower alkoxycarbonylmethylamino, hydroxycarbonylmethylamino, anilino optionally substituted by a halogen atom, 2-pyridylamino, —O—cation or halogen atom.

We have had a great interest in investigating the usability as herbicide of isoxazolidine derivatives and synthesized and tested a variety of isoxazolidine derivatives on their herbicidal activity. As a result, we have now found that new 2-(substituted-phenoxy)propionic acid derivatives having general formula (I) undermentioned exhibit a high herbicidal activity.

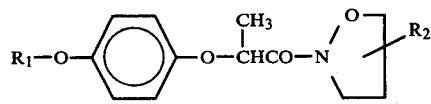 (I)

where $R_1$ is 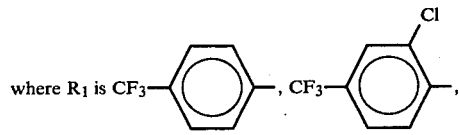

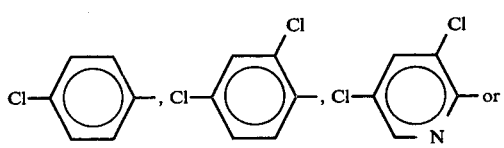

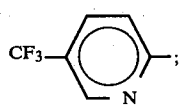;

and $R_2$ is a hydrogen atom or a lower alkyl group.

BRIEF SUMMARY OF THE INVENTION

According to one aspect of this invention, therefore, there are provided 2-(substituted-phenoxy)propionic acid derivatives having general formula (I) above.

According to another aspect of this invention, there is provided a process of inhibiting the growth of unwanted plants which comprises applying to the plants or to the locus thereof a herbicidal amount of at least one compound of general formula (I) above.

In a further aspect of this invention, there is provided a herbicidal composition comprising as an active ingredient at least one compound of general formula (I) above, in admixture with a solid or liquid diluent or carrier.

DETAILED DESCRIPTION OF THE INVENTION

The isoxazolidine derivatives of 2-(substituted-phenoxy)propionic acids of general formula (I) according to this invention (hereinafter referred to as compounds according to this invention) have never been described in literature, but are new compounds. We have found that the compounds according to this invention are superior to the known herbicidal compounds referred to above both in their herbicidal activity and in their phytotoxicity against crop plants. Thus, the compounds according to this invention, whether they are applied to soil or stalks and leaves (i.e. plants themselves), exhibit an excellent herbicidal activity against weeds, particularly graminaceous weeds, while they have little or no phytotoxicity to broad leaved crop plants such as soya bean, beet, radish and cabbage and cotton plants and also have no toxicity to men and beasts as well as to fishes, so that they can be utilized safely for the intended purposes.

The compounds of formula (I) according to this invention have a pair of optical antiposes, i.e. d- and l-isomers, as in the known compounds of similar structure as above referred to. It is often usual that physiological activity of d- or l-optically active isomer is higher than that of optically inactive racemic compound. This also apply to the compounds according to this invention, that is the d-isomer of the compounds has a higher herbicidal activity than that of the racemic compound. Needless to say, however, the compounds according to this invention may be used as a herbicide in any form of d-isomer, l-isomer and mixtures of d- and l-isomers in desired proportions.

Typical examples of the compounds according to this invention are listed in Table 1 below:

TABLE 1
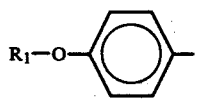
| Compound No. | R₁ | 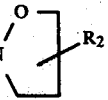 | Nature of isomer | Physical properties Melting point or Refractive index | Optical rotation |
|---|---|---|---|---|---|
| 1 | 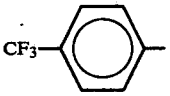 |  | dl | mp. 105~107° C. | |
| 2 | " | " | d | $n_D^{20} = 1.5315$ | $\alpha_D^{20} = -22.9°$ |
| 3 | " | 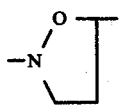 | dl | mp. 115~119° C. | |
| 4 | " | 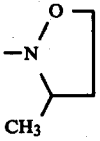 | " | mp. 79.5~81.0° C. | |
| 5 | 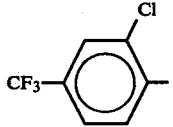 |  | " | mp. 66.5~67.5° C. | |
| 6 | " | " | d | $n_D^{20} = 1.5374$ | $\alpha_D^{20} = -19.1°$ |
| 7 | " | 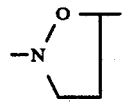 | dl | $n_D^{20} = 1.5365$ | |
| 8 | " | 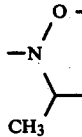 | " | $n_D^{20} = 1.5351$ | |
| 9 | 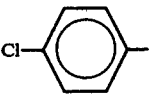 |  | " | mp. 98~100° C. | |
| 10 | " | 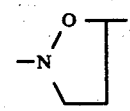 | " | mp. 95~98° C. | |
| 11 | 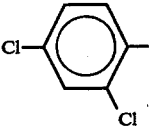 |  | " | mp. 115~118° C. | |

TABLE 1-continued $$R_1-O-\underset{}{\bigcirc}-O-\underset{CH_3}{\overset{|}{C}HCO}-N\overset{O}{\underset{}{\diagdown\diagup}}R_2$$

| Compound No. | R₁ | $-N\overset{O}{\diagdown\diagup}R_2$ | Nature of isomer | Physical properties Melting point or Refractive index | Optical rotation |
|---|---|---|---|---|---|
| 12 | Cl-⬡-Cl | $-N\overset{O}{\diagdown\diagup}$ | d | mp. 113~117° C. | $\alpha_D^{20} = -14.6°$ |
| 13 | " | $-N\overset{O}{\diagdown\diagup}-CH_3$ | dl | mp. 70~72° C. | |
| 14 | Cl-⬡(N)-Cl | $-N\overset{O}{\diagdown\diagup}$ | dl | mp. 105.0~107.5° C. | |
| 15 | " | " | d | mp. 93~94° C. | $\alpha_D^{20} = -3.3°$ |
| 16 | " | $-N\overset{O}{\diagdown\diagup}-CH_3$ | dl | mp. 103~105° C. | |
| 17 | CF₃-⬡(N) | $-N\overset{O}{\diagdown\diagup}$ | " | mp. 83~85° C. | |
| 18 | " | $-N\overset{O}{\diagdown\diagup}-CH_3$ | " | mp. 94~97° C. | |

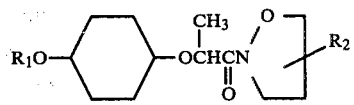

(I)

Compounds of formula (I) according to this invention in which R₁ has any of the meanings as defined above and R₂ is hydrogen atom are most preferred.

Compounds of formula (I) according to this invention may be prepared by any of the processes of Reactions (a), (b) and (c) as undermentioned. These processes are applicable to the preparation of those compounds either in the racemic mixture and in an optical isomer.

Reaction (a):

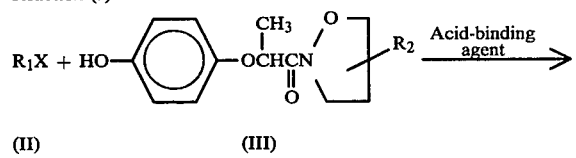

In general formula (II), R₁ has the same meaning as defined above and X is a halogen atom. Compounds of formula (II) are already known and may be easily prepared by a known process. In general formula (III), R₂ has the same meaning as defined above. Compounds of formula (III) are new compounds per se and may be easily prepared by reacting an N-(2-halopropionyl)isoxazolidine or an N-[(2-tosyloxy)propionyl]isoxazolidine with hydroquinone as shown in Example 3 or Example 4 hereinafter given, respectively. The preparation of N-(2-halopropionyl)isoxazolidine and N-[(2-tosyloxy)-propionyl]isoxazolidine is shown in Examples 1 and 2 hereinafter given, respectively, for reference.

The reaction of compound (II) with compound (III) according to Reaction (a) is carried out preferably in an organic solvent. Examples of organic solvents which may be used include hydrocarbons such as benzene and toluene, halogenated hydrocarbons such as chloroform, carbon tetrachloride and dichloroethane, ethers such as ethyl ether and tetrahydrofuran, esters such as methyl acetate and ethyl acetate, ketones such as acetone and methyl isobutyl ketone, nitriles such as acetonitrile and propionitrile, amides such as dimethylformamide and N-methylformamide and dimethylsulfoxide. The reaction is preferably carried out in the presence of an acid-binding agent such as an organic amine, e.g. triethylamine and pyridine, and an inorganic base, e.g. potassium carbonate and sodium or potassium hydroxide. Compound of formula (III) may also be used in the form of sodium or potassium salt which may be prepared by reacting compound (III) with metallic sodium, metallic potassium, sodium hydride or sodium amide.

The reaction between compound (II) and compound (III) may proceed even at room temperature, but is usually carried out at a temperature between a slightly higher temperature than room temperature and the boiling point of the solvent used to conduct the reaction at a higher rate. In case an acid-binding agent is used, the salt of said acid-binding agent deposited during the reaction is filtered off and the filtrate is distilled to remove the solvent and to yield the desired compound. Alternatively, the desired compound is recovered from the reaction mixture by adding to the mixture an organic solvent such as benzene, chloroform, ethyl ether or tetrahydrofuran and water, separating the organic layer from the aqueous layer and distilling the organic solvent off. The preparation of compounds of formula (I) according to Reaction (a) is exemplified later in Examples 5 to 8.

Reaction (b):

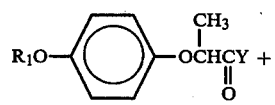

(IV)

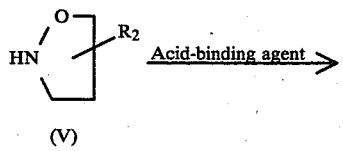

(V)

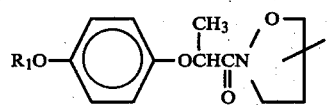

(I)

In general formula (IV), $R_1$ has the same meaning as defined above and Y is a halogen atom. Compounds of formula (IV) may easily be prepared by reacting the corresponding acids which are known as described in Japanese patent application KOKAI Sho 52-83618, Sho 52-128377 and Sho 54-122728 and Japanese patent Publication No. 8727/79 with a halogenating agent such as a thionyl halide and phosphoryl trichloride.

In general formula (V), $R_2$ has the same meaning as defined above. Compounds of formula (V) may be prepared by a process known per se, for example by a process comprising reacting a hydroxyurethane with a 1,3-dihaloalkane to yield a carbamate having an isoxazolidine ring and hydrolyzing the carbamate with an aqueous mineral acid to afford the desired compound in the form of a mineral acid salt.

The reaction between compound (IV) and compound (V) according to Reaction (b) is usually carried out in an organic solvent. As in Reaction (a), the organic solvent to be used may be hydrocarbons, halogenated hydrocarbons, ethers, esters, ketones, nitriles, amides and the like. Similarly, an acid-binding agent such as an organic amine, e.g. triethylamine and pyridine, and an inorganic base such as potassium carbonate and sodium hydroxide, may be used. The reaction may proceed rapidly at such a low temperature as under ice-cooling, water-cooling and at room temperature, so that no positive heating is usually necessary. After the completion of the reaction, the reaction mixture may be treated in the same manner as in the case of Reaction (a) to yield the desired compound. The preparation of compounds of formula (I) according to Reaction (b) is exemplified later in Examples 9 to 11. Reaction (c):

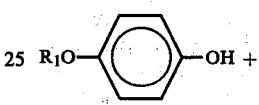

(VI)

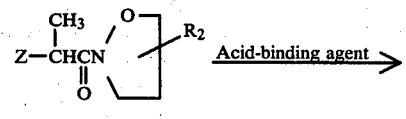

(VII)

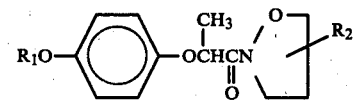

(I)

In general formula (VI), $R_1$ has the same meaning as defined above. Compounds of formula (VI) are already known and may be prepared easily, for example, by reacting a 1-halogeno-4-(trifluoromethyl)benzene, a 1,2-dihalogeno-4-(trifluoromethyl)benzene, a 3,5-dichloro-2-pyridylhalide or a 5-trifluoromethyl-2-pyridylhalide with hydroquinone.

In general formula (VII), $R_2$ has the same meaning as defined above and Z is a halogen atom or a tosyloxy group. Compounds of formula (VII) are new compounds and may be prepared by reacting a 2-halo- or 2-tosyloxypropionyl halide with an isoxazolidine as shown in Examples 1 and 2 hereinafter given for reference.

The reaction between compound (VI) and compound (VII) according to Reaction (c) may usually be conducted in an organic solvent. Organic solvents suitable to use here may be those exemplified for use in Reaction (a). Similarly, an acid-binding agent is preferably used for Reaction (c), too. Examples of such acid-binding agent include those concretely given for use in Reaction (a). The reaction may proceed even at room temperature, but is preferably carried out at a temperature between a slightly higher temperature than room temperature and the boiling point of the solvent used to conduct the reaction at a higher rate. After the completion of the reaction, the reaction mixture may be treated in the same manner as in the case of Reaction (a) to yield the desired compound. The preparation of compounds of formula (I) according to Reaction (c) is exemplified later in Examples 12 to 16.

The compounds according to this invention are useful both as pre- and post-emergence herbicides. Thus, when used as pre-emergence herbicides, the compounds may usually be applied to the soil in which a crop is to be planted, before or during seeding or after seeding and before emergence of the crop and before emergence of weeds. As post-emergence herbicides, they may usually be applied directly to the stalks and leaves of the weeds to be killed.

The compounds according to this invention, when used as herbicides, are preferably applied in the form of a composition in which the active ingredient is mixed with a solid or liquid diluent or carrier.

The herbicidal composition according to this invention may be for example in the form of aqueous solution, dispersion, emulsion, dusting powder, wettable powder, flowable powder (sol), driftless (DL-type) powder, granules, fine granules, tablets and others. Any form of the composition above-mentioned may be prepared according to conventional formulation techniques. Any desired solid or liquid carrier or diluent which has been used conventionally in the preparation of agricultural or horticultural chemical composition.

Suitable solid carriers or diluents include mineral powders such as kaolin, bentonite, clay, montmorillonite, talc, diatomaceous earth, mica, vermiculite, gypsum, calcium carbonate, apatite, white carbon, slaked lime, siliceous sand, ammonium sulfate and urea; vegetable powders such as soya bean flour, wheat flour, wood meal, tobacco powder, starch and crystalline cellulose; macromolecular compounds such as petroleum resin, polyvinyl chloride, ketone resin and dammar gum; alumina, silicates, sugar polymers, high-dispersible silicic acid and waxes.

Suitable liquid carriers or diluents include water; alcohols such as methanol, ethanol, n-propanol, i-propanol, butanol, ethylene glycol and benzyl alcohol, aromatic hydrocarbons such as toluene, benzene, xylene, ethylbenzene, chlorobenzene and methyl naphthalene; halogenated hydrocarbons such as chloroform, carbon tetrachloride, dichloromethane, chloroethylene, monochlorobenzene, trichlorofluoromethane and dichlorodifluoromethane; ethers such as ethylether, ethylene oxide, dioxane and tetrahydrofuran; ketones such as acetone, methyl ethyl ketone, cyclohexanone, methyl isobuty ketone and isophorone; esters such as ethyl acetate, butyl acetate, ethylene glycol acetate and amyl acetate; acid amides such as dimethylformamide and dimethylacetamide; nitriles such as acetonitrile, propionitrile and acrylonitrile; sulfoxides such as dimethylsulfoxide; alcoholethers such as ethylene glycol monomethylether and ethylene glycol monoethylether; aliphatic and cycloaliphatic hydrocarbons such as n-hexane and cyclohexane; industrial gasoline such as petroleum ether and solvent naphtha; and petroleum fractions such as paraffins, kerosene and gas oil.

In the preparation of emulsion, dispersion, wettable powder, flowable powder and the like, one or more surface active agents are used for the purpose of emulsification, dispersion, solubilization, wetting, foaming, lubrication, spreading or the like. Surface active agents may be of non-ionic, anionic, cationic or amphoteric type. Suitable agents of the non-ionic type include for example polyoxyethylene alkylethers, polyoxyethylene alkylesters, polyoxyethylenesorbitan alkylesters and sorbitan alkylesters. Suitable agents of the anionic type include for example soaps, alkylbenzene sulfonates, alkylsulfosuccinates, alkyl sulphates, polyoxyethylene alkylsulfates and aryl sulfonates. Suitable agents of the cationic type include alkylamines such as laurylamine, stearyl trimethyl ammonium chloride and alkyl dimethyl benzyl ammonium chloride; and polyoxyethylene alkylamines. Suitable agents of the amphoteric type include carboxylic acids of betaine type and salts of sulfuric esters.

In addition to the carriers or diluents and surface active agents, the herbicidal composition may contain a variety of additives, as desired. Such additives include for example polyvinyl alcohol, carboxymethylcellulose, gum arabic, polyvinyl acetate, gelatine, casein, sodium alginate and tragacanth gum.

The herbicidal compositions according to this invention may be formulated in any desired form as exemplified above in which the compound of formula (I) is present in an amount of 0.1 to 95% by weight, preferably 0.5 to 90% by weight. For example, the content of the compounds of formula (I) may usually be 0.1 to 5% by weight when formulated in the form of powder, DL powder or fine granules (F), 1 to 10% by weight in the form of granules, and 5 to 95% by weight in the form of wettable powder, aqueous emulsion or solution.

The herbicidal compositions in the form of, for example, granules may be applied as such by dusting them on the surface of or in the soil or in aquatic medium in an amount of about 2 to 5 kg of the composition per 10 ares (about 5 to 1000 g of the active ingredient per 10 ares). In cases of aqueous solutions, emulsions or wettable powder, the compositions are usually diluted about 500 to 2000 times with water or an appropriate solvent whereby to give a concentration of about 5 to 1000 ppm, preferably about 50 to 500 ppm of the active ingredient and the diluted compositions are applied at a rate of about 100 to 300 l per 10 ares (about 5 to 1000 g of the active ingredient per 10 ares).

When the compounds of this invention, as such or in the form of a composition, are used as herbicides, they may be used, if desired, in combination with one or more of known herbicides, insecticides, fungicides, plant-growth regulating agents and others for extending the application range of the compounds with a possibility of synergism resulting from such combinations in some cases.

Examples of other herbicides which may be used in combination with the compounds of this invention include triazine herbicides such as 2-chloro-4-ethylamino-6-isopropylamino-1,3,5-triazine, 2-chloro-4,6-bis(ethylamino)-1,3,5-triazine, 2-methylthio-4-ethylamino-6-isopropylamino-1,3,5-triazine, 2,4-bis(isopropylamino)-6-methylthio-1,3,5-triazine, 2-(4-chloro-6-ethylamino)-1,3,5-triazin-2-ylamino)-2-methylpropionitrile, 4-amino-6-tert-butyl-4,5-dihydro-3-methylthio-1,2,4-triazin-5-one, 3-cyclohexyl-6-dimethylamino-1-methyl-1,3,5-triazin-2,4-dione, 4-amino-4,5-dihydro-3-methyl-6-phenyl-1,2,4-triazin-5-one and 6-tert-butyl-4-isobutylideneamino-3-methylthio-1,2,4-triazin-5-one; urea herbicides such as 3-(3,4-dichlorophenyl)-1-methoxy-1-methylurea, 3-(4-chlorophenyl)-1,1-dimethylurea, 3-(3,4-dichlorophenyl)-1,1-dimethylurea, 1,1-dimethyl-3-($\alpha,\alpha,\alpha$-trifluoro-meta-tolyl)urea, 3-(4-isopropylphenyl)-1,1-dimethylurea, 3-[4-(4-chlorophenoxhydroquinone (12.1 g), anhydrous potassium carbonate (29.0 g) and acetonitrile (100 ml) was heated under reflux with stirring for 3 hours. After cooling, the reaction mixture was filtered through a suction filter to remove solid matters and the filtrate was concentrated in vacuo. The residue was washed with the addition of chloroform and 1 N hydrochloric acid and the organic layer separated was washed with a 5% aqueous sodium bicarbonate solution and dried over anhydrous sodium sulfate. Removal of the solvent by a distillation in vacuo gave N-[d-(−)-2-(4-hydroxyphenoxy)propionyl]isoxazolidine (20.4 g) as a pale yellow oil which was purified by silica gel column chromatography to yield a colorless oil. The oil crystallized soon upon standing at room temperature. Recrystallization from a mixture of n-hexane and benzene afforded a white crystalline solid. m.p. 119°–124° C., $a_D^{20} = +21.7°$.

EXAMPLE 5

Preparation of Compound No. 5 (Reaction (a))

A mixture of 1,2-dichloro-3-(trifluoromethyl)benzene (21.5 g), N-[(±)-2-(4-hydroxyphenoxy)propionyl]isoxazolidine (23.7 g) which was prepared as in Example 3, anhydrous potassium carbonate (14.5 g) and dimethylsulfoxide (200 ml) was stirred at 130° C. for 3 hours. After the mixture was cooled, water and benzene were added thereto to form two layers. The organic layer thus separated was washed with 1 N aqueous sodium hydroxide solution and then with water and dried over anhydrous sodium sulfate. Removal of the solvent by a distillation in vacuo gave N-[(±)-2-[4-(2-chloro-4-trifluoromethylphenoxy)phenoxy]propionyl]isoxazolidine (39.9 g) as a pale brown crystalline solid. Recrystallization from a mixture of n-hexane and ethyl acetate afforded a white crystalline solid. m.p. 66.5°–67.5° C.

EXAMPLE 6

Preparation of Compound No. 6 (Reaction (a))

A mixture of 1,2-dichloro-4-(trifluoromethyl)benzene (21.5 g), N-[d-(+)-2-(4-hydroxyphenoxy)propionyl]isoxazolidine (23.7 g) which was prepared as in Example 4, potassium carbonate (6.6 g) and dimethylsulfoxide (200 ml) was stirred at 120° C. for 5 hours. After the reaction mixture was cooled, water and benzene were added thereto whereby to form two layers. The organic layer thus separated was washed with water and dried over anhydrous sodium sulfate. Removal of the solvent by a distillation in vacuo gave N-[d-(+)-2-[4-(2-chloro-4-trifluoromethylphenoxy)phenoxy]propionyl]isoxazolidine (38.6 g) as a pale brown oil. Purification by silica gel column chromatography yielded a colorless oil. $n_D^{20} = 1.5374$, $a_D^{20} = -19.1°$.

EXAMPLE 7

Preparation of Compound No. 11 (Reaction (a))

A mixture of 2,4-dichloro-bromobenzene (22.6 g), N-[(±)-2-(4-hydroxyphenoxy)propionyl]isoxazolidine (23.7 g) which was prepared as in Example 3, anhydrous potassium carbonate (14.5 g) and dimethylsulfoxide (200 ml) was stirred at 120° C. for 4 hours. After the reaction mixture was cooled, water and benzene were added thereto whereby to form two layers. The organic layer so separated was washed with 1 N aqueous sodium hydroxide solution and then with water and dried over anhydrous sodium sulfate. Removal of the solvent by a distillation in vacuo gave N-[(±)-2-[4-(2,4-dichlorophenoxy)phenoxy]propionyl]isoxazolidine (30.9 g) as a pale yellow crystalline solid. Recrystallization from a mixture of n-hexane/ethyl acetate yielded a white crystalline solid. m.p. 115°–118° C.

EXAMPLE 8

Preparation of Compound No. 14 (Reaction (a))

A mixture of 2,3,5-trichloropyridine (18.3 g), N-[(±)-2-(4-hydroxyphenoxy)propionyl]isoxazolidine (23.7 g) which was prepared as in Example 3, anhydrous potassium carbonate (14.5 g) and dimethylsulfoxide (200 ml) was stirred at 120° C. for 4 hours. To the reaction mixture, after cooling, were added water and benzene whereby to form two layers. The organic layer so separated was washed with 1 N aqueous sodium hydroxide solution and then with water and dried over anhydrous sodium sulfate. Removal of the solvent by a distillation in vacuo gave N-[(±)-2-[4-(3,5-dichloro-2-pyridyloxy)phenoxy]propionyl]isoxazolidine (31.4 g) as a pale yellow crystalline solid. Recrystallization from a mixture of n-hexane/ethyl acetate yielded a white crystalline solid. m.p. 105.5°–107.5° C.

EXAMPLE 9

Preparation of Compound No. 1 (Reaction (b))

To a mixture of isoxazolidine hydrochloride (11.0 g) and chloroform (200 ml), under stirring and ice-cooling, was added (±)-2-[4-(4-trifluoromethylphenoxy)phenoxy]propionyl chloride (34.5 g) and then added dropwise triethylamine (22.2 g). After the completion of addition, the reaction mixture was stirred for further 30 minutes at room temperature, to which water was added to form two layers. The organic layer so separated was washed with 1 N hydrochloric acid and then with 1 N aqueous sodium hydroxide and dried over anhydrous sodium sulfate. Removal of the solvent by a distillation in vacuo gave N-[(±)-2-[4-(4-trifluoromethylphenoxy)phenoxy]propionyl]isoxazolidine (37.3 g) as a white crystalline solid. After recrystallization from a mixture of n-hexane/acetone, the resulting white crystalline solid showed the melting point of 105°–107° C.

EXAMPLE 10

Preparation of Compound No. 13 (Reaction (b))

To a mixture of 5-methylisoxazolidine hydrochloride (13.6 g) and chloroform (200 ml), under stirring and ice-cooling, was added (±)-2-[4-(2,4-dichlorophenoxy)phenoxy]propionyl chloride (34.6 g) and then added dropwise triethylamine (22.2 g). After the completion of addition, the reaction mixture was stirred for further 30 minutes at room temperature, to which water was added to form two layers. The organic layer so separated was washed with 1 N hydrochloric acid and then with 1 N aqueous sodium hydroxide solution and dried over anhydrous sodium sulfate. Removal of the solvent by a distillation in vacuo gave N-[(±)-2-(2,4-dichlorophenoxy)phenoxy]propionyl]-5-methylisoxazolidine (38.4 g) as a pale yellow crystalline solid. Recrystallization from a mixture of n-hexane/ethyl acetate yielded a white crystalline solid. m.p. 70°–72° C.

EXAMPLE 11

Preparation of Compound No. 18 (Reaction (b))

To a mixture of 5-methylisoxazolidine hydrochloride (13.6 g) and chloroform (200 ml), under stirring and ice-cooling, was added (±)-2-[4-(5-trifluoromethyl-2-pyridyloxy)phenoxy]propionyl chloride (34.6 g) and y)phenyl]-1,1-dimethylurea, 1-(benzothiazol-2-yl)-3-methylurea, 1-(benzothiazol-2-yl)-1,3-dimethylurea and 1-(5-tert-butyl-1,3,4-thiadiazol-2-yl)-1,3-dimethylurea; carbamate herbicides such as isopropyl 3-chlorophenylcarbamate, 1-methylprop-2-ynyl-3-chlorocarbanylate, methyl 3-meta-tolylcarbamoyloxyphenylcarbamate, methyl 4-aminophenylsulfonylcarbamate, S-ethyl diisobutylthiocarbamate, S-ethyl dipropylthiocarbamate, S-(4-chloro)benzyl diethylthiocarbamate, S-ethyl N-cyclohexyl-N-ethylthiocarbamate and S-2,3,3-trichloroallyl diisopropylthiocarbamate; toluidine herbicides such as α,α,α-trifluoro-2,6-dinitro-N,N-dipropyl-para-toluidine, N-(2-chloroethyl)-α,α,α-trifluoro-2,6-dinitro-N-propyl-para-toluidine, N-(1-ethylpropyl)-2,6-dinitro-3,4-xylidine and N-(cyclopropylmethyl)-α,α,α-trifluoro-2,6-dinitro-N-propyl-para-toluidine; diphenylether herbicides such as methyl 5-(2,4-dichlorophenoxy)-2-nitrobenzoate, sodium 5-[2-chloro-4-(trifluoromethyl)-phenoxy]-2-nitrobenzoate and 2-chloro-1-(3-ethoxy-4-nitrophenoxy)-4-(trifluoromethyl)benzene; phenoxyaliphatic acid herbicides such as 2,4-dichlorophenoxyacetic acid and its salts and esters such as methyl, ethyl and butyl esters, S-ethyl 4-chloro-2-methylphenoxythioacetate, 2-(4-chloro-2-methyl-phenoxypropionic acid and its salts, methyl 2-[4-(2,4-dichlorophenoxy)phenoxy]propionate and butyl 2-[4-(5-trifluoromethyl-2-pyridyloxy)phenoxy]propionate; amide herbicides such as 2-chloro-2',6'-diethyl-N-(methoxymethyl)acetanilide, 2-chloro-N-(2-ethyl-6-methylphenyl)-N-(2-methoxy-1-methylethyl)acetamide, 3',4'-dichlorophenylpropionanilide, N-1-naphthylphthalamic acid and N-benzoyl-N-(3,4-dichlorophenyl)-D,L-alaninate; diazine herbicides such as 5-tert-butyl-3-(2,4-dichloro-5-isopropoxyphenyl)-1,3,4-oxadiazol-2-one, 2-(3,4-dichlorophenyl)-4-methyl-1,2,4-oxadiazolin-2,5-dione and 3-isopropyl-(1H)-2,1,3-benzothiadiazin-4(3H)-one-2,2-dioxide; organophosphorus herbicides such as O-ethyl O-(6-nitro-meta-tolyl) sec-butylphosphoroamidothioate, N-(phosphonomethyl)glycine and 2-amino-4-(methylphosphinobutyryl)-alanylalanine monosodium salt; benzoic acid herbicides such as 3-amino-2,5-dichlorobenzoic acid and dimethyl tetrachloroterephthalate; nitrile herbicides such as 2,6-dichlorobenzonitrile and 4-hydroxy-3,5-diiodobenzonitrile; uracil herbicides such as 5-bromo-3-sec-butyl-6-methyluracil and 3-cyclohexyl-6,7-dihydro-1H-cyclopentapyrimidin-2,4-dione; pyridinium salt herbicides such as 1,1'-dimethyl-4,4'-bipyridinium salts and 1,1'-ethylene-2,2'-bipyridinium salts; arsenic herbicides such as disodium methanearsonate and monosodium methanearsonate; and other herbicides such as 2-sec-butyl-4,6-dinitrophenol, 7-oxabicyclo[2,2,1]heptane-2,3-dicarboxylic acid, 4-chloro-2-oxobenzothiazolin-3-ylacetic acid, methyl 3[1-(allyloxyimino)butyl]-4-hydroxy-6,6-dimethyl-2-oxocyclohex-3-ene carboxylate and 2-[1-(ethoxyimino)butyl]-5-[2-(ethylthio)propyl]-3-hydroxy-2-cyclohexen-1-one.

This invention is now illustrated, but not limited, by the following Examples. Examples 1 to 4 are given by way of reference and are illustrative of the preparation of some of starting materials to be used for the preparation of the compounds of this invention. Examples 5 to 16 are illustrative of the preparation of the compounds of formula (I) according to this invention. Examples 17 to 25 are illustrative of the herbicidal compositions of this invention. Examples 26 to 29 are illustrative of the herbicidal properties of the compounds of this invention. In Examples, all parts and percentages are by weight unless otherwise stated.

EXAMPLE 1

Preparation of N-[(±)-2-chloropropionyl]isoxazolidine

To a mixture of isoxazolidine hydrochloride (11.0 g) and chloroform (200 ml) was added (±)-2-chloropropionyl chloride (13.3 g) under ice-cooling and stirring and then added dropwise triethylamine (22.2 g) under the same conditions. The stirring was continued at room temperature for further one hour, after which an amount of water was added to the reaction mixture to form layers. The organic layer thus separated was washed with 1 N hydrochloric acid and then with a 5% aqueous sodium bicarbonate solution and dried over anhydrous sodium sulfate. Removal of the solvent by a distillation in vacuo gave N-[(±)-2-chloropropionyl]isoxazolidine (15.0 g) as a pale yellow oil. Purification of the oil by silica gel column chromatography afforded a colorless oil. $n_D^{20} = 1.4918$.

EXAMPLE 2

Preparation of N-[l-(−)-(2-tosyloxy)propionyl]isoxazolidine

To a mixture of isoxazolidine hydrochloride (11.0 g) and chloroform (200 ml), was added l-(−)-(2-tosyloxy)-propionyl chloride (26.3 g) and then added dropwise triethylamine (22.2 g) under ice-cooling and stirring. The stirring was continued at room temperature for further 20 minutes, after which an amount of water was added to the reaction mixture to form layers. The organic layer thus separated was washed with 1 N hydrochloric acid and then with a 5% aqueous sodium bicarbonate solution and dried over anhydrous sodium sulfate. Removal of the solvent by a distillation in vacuo gave N-[l-(−)-(2-tosyloxy)propionyl]isoxazolidine (28.7 g) as a pale yellow oil which crystallized soon upon standing. Recrystallization from a mixture of n-hexane and ethyl acetate gave a white crystalline solid. m.p. 61°–62° C., $\alpha_D^{20} = -32.7°$.

EXAMPLE 3

Preparation of N-[(±)-2-(4-hydroxyphenoxy)propionyl]isoxazolidine (a compound of formula (III))

A mixture of N-[(±)-2-chloropropionyl]isoxazolidine (16.4 g) which was prepared as in Example 1, hydroquinone (13.2 g), anhydrous potassium carbonate (29.0 g) and dimethylformamide (100 ml) was stirred at 120° C. for 2 hours. After cooling, the reaction mixture was filtered through a suction filter to remove solid matters and the filtrate was concentrated in vacuo. The residue was washed with the addition of chloroform and 1 N hydrochloric acid and then with water and dried over anhydrous sodium sulfate. Removal of the solvent by a distillation in vacuo gave N-[(±)-2-(4-hydroxyphenoxy)propionyl]isoxazolidine (21.6 g) as a pale yellow oil which was purified by silica gel column chromatography to yield a colorless oil. $n_D^{20} = 1.5412$.

EXAMPLE 4

Preparation of N-[d-(+)-2-(4-hydroxyphenoxy)propionyl]isoxazolidine (a compound of formula (III))

A mixture of N-[l-(−)-(2-tosyloxy)propionyl]isoxazolidine (29.9 g) which was prepared as in Example 2, then added dropwise triethylamine (22.2 g). After the completion of addition, the reaction mixture was stirred for further 30 minutes at room temperature, to which water was added to form two layers. The organic layer so separated was washed with 1 N hydrochloric acid and then with 1 N aqueous sodium hydroxide solution and dried over anhydrous sodium sulfate. Removal of the solvent by a distillation in vacuo gave N-[(±)-2-[4-(5-trifluoromethyl-2-pyridyloxy)phenoxy]propionyl]-5-methylisoxazolidine (38.0 g) as a white crystalline solid which showed the melting point of 94°–97° C. after recrystallization from a mixture of n-hexane/acetone.

EXAMPLE 12

Preparation of Compound No. 2 (Reaction (c))

A mixture of 4-(4-trifluoromethyl)phenoxyphenol (25.4 g), N-[l-(−)-2-tosyloxypropionyl]isoxazolidine (15.0 g) which was prepared as in Example 2, anhydrous potassium carbonate (15.2 g) and acetonitrile (300 ml) was heated under reflux with stirring for 5 hours. After cooling, the reaction mixture was filtered through a suction filter to remove solid matters and the filtrate was concentrated in vacuo. The residue was washed with the addition of water and benzene and the organic layer formed was separated and dried over anhydrous sodium sulfate. The removal of the solvent by a distillation in vacuo gave N-[d-(−)-2-[4-(4-trifluoromethylphenoxy)phenoxy]propionyl]isoxazolidine (36.8 g) as a pale brown oil. Purification by silica gel column chromatography yielded a colorless oil. $n_D^{20}=1.5315$, $\alpha_D^{20}=-22.9°$.

EXAMPLE 13

Preparation of Compound No. 9 (Reaction (c))

A mixture of 4-(4-chlorophenoxy)phenol (22.1 g), N-[(±)-2-chloropropionyl]isoxazolidine (16.4 g) which was prepared as in Example 1, anhydrous potassium carbonate (15.2 g) and acetonitrile (300 ml) was heated under reflux with stirring for 5 hours. After cooling, the reaction mixture was filtered through a suction filter to remove solid matters and the filtrate was concentrated in vacuo. The residue was washed with the addition of water and benzene and the organic layer formed was separated and dried over anhydrous sodium sulfate. The removal of the solvent by a distillation in vacuo gave N-[(±)-2-[4-(4-chlorophenoxy)phenoxy]propionyl]isoxazolidine (33.4 g) as a pale yellow crystalline solid. Recrystallization from a mixture of n-hexane/ethyl acetate yielded a white crystalline solid. m.p. 98°–100° C.

EXAMPLE 14

Preparation of Compound No. 12 (Reaction (c))

A mixture of 4-(2,4-dichlorophenoxy)phenol (25.5 g), N-[l-(−)-2-tosyloxypropionyl]isoxazolidine (30.0 g) which was prepared as in Example 2, anhydrous potassium carbonate (15.2 g) and acetonitrile (300 ml) was heated under reflux with stirring for 5 hours. After cooling, the reaction mixture was filtered through a suction filter to remove solid matters and the filtrate was concentrated in vacuo. The residue was washed with the addition of water and benzene and the organic layer formed was separated and dried over anhydrous sodium sulfate. The removal of the solvent by a distillation in vacuo gave N-[d-(−)-2-[4-(2,4-dichlorophenoxy)phenoxy]propionyl]isoxazolidine (34.4 g) as a pale yellow crystalline solid. Recrystallization from a mixture of n-hexane/ethyl acetate yielded a white crystalline solid. m.p. 113°–117° C., $\alpha_D^{20}=-14.6°$.

EXAMPLE 15

Preparation of Compound No. 17 (Reaction (c))

A mixture of 4-(5-trifluoromethyl-2-pyridyloxy)phenol (25.6 g), N-[(±)-2-chloropropionyl]isoxazolidine (16.4 g) which was prepared as in Example 1, anhydrous potassium carbonate (15.2 g) and acetonitrile (300 ml) was heated under reflux with stirring for 5 hours. After cooling, the reaction mixture was filtered through a suction filter to remove solid matters and the filtrate was concentrated in vacuo. The residue was washed with the addition of water and benzene and the organic layer formed was separated and dried over anhydrous sodium sulfate. The removal of the solvent by a distillation in vacuo gave N-[(±)-2-[4-(5-trifluoromethyl-2-pyridyloxy)phenoxy]propionyl]isoxazolidine (35.5 g) as a pale yellow crystalline solid. Recrystallization from a mixture of n-hexane/ethyl acetate yielded a white crystalline solid. m.p. 83°–85° C.

EXAMPLE 16

Preparation of Compound No. 15 (Reaction (c))

A mixture of 4-(3,5-dichloro-2-pyridyloxy)phenol (25.6 g), N-[l-(−)-2-tosyloxypropionyl]isoxazolidine (30.0 g) which was prepared as in Example 2, anhydrous potassium carbonate (15.2 g) and acetonitrile (300 ml) was heated under reflux with stirring for 5 hours. After cooling, the reaction mixture was filtered through a suction filter to remove solid matters and the filtrate was concentrated in vacuo. The residue was washed with the addition of water and benzene and the organic layer formed was separated and dried over anhydrous sodium sulfate. The removal of the solvent by a distillation in vacuo gave N-[d-(−)-2-[4-(3,5-dichloro-2-pyridyloxy)phenoxy]propionyl]isoxazolidine (34.9 g) as a pale yellow crystalline solid. Recrystallization from a mixture of n-hexane/acetone yielded a white crystalline solid. m.p. 93°–94° C., $\alpha_D^{20}=-3.3°$.

EXAMPLE 17

Preparation of wettable powder

Compound No. 1 (20 parts), polyoxyethylene alkylarylether (5 parts), calcium lignosulfonate (3 parts) and diatomaceous earth (72 parts) are ground and mixed together homogeneously to give a wettable powder containing 20% of the active compound. This may be diluted with water upon use and applied at a rate of 5–1000 g of the active compound per 10 ares.

EXAMPLE 18

Preparation of wettable powder

Compound No. 9 (20 parts), polyoxyethylene alkylarylether (5 parts), calcium lignosulfonate (3 parts) and diatomaceous earth (72 parts) are ground and mixed together homogeneously to give a wettable powder containing 20% of the active compound. This may be diluted with water upon use and applied at a rate of 5–1000 g of the active compound per 10 ares.

EXAMPLE 19

Preparation of wettable powder

Compound No. 14 (20 parts), polyoxyethylene alkylarylether (5 parts), calcium lignosulfonate (3 parts)

and diatomaceous earth (72 parts) are ground and mixed together homogeneously to give a wettable powder containing 20% of the active compound. This may be diluted with water upon use and applied at a rate of 5–1000 g of the active compound per 10 ares.

EXAMPLE 20

Preparation of emulsifiable concentrate

Compound No. 5 (40 parts), xylene (40 parts) and polyoxyethylene alkylarylether (20 parts) are homogeneously mixed together to give a emulsifiable concentrate containing 40% of the active compound. This may be diluted with water upon use and applied at a rate of 5–1000 g of the active compound per 10 ares.

EXAMPLE 21

Preparation of emulsifiable concentrate

Compound No. 13 (40 parts), xylene (40 parts) and polyoxyethylene alkylarylether (20 parts) are homogeneously mixed together to give a emulsifiable concentrate containing 40% of the active compound. This may be diluted with water upon use and applied at a rate of 5–1000 g of the active compound per 10 ares.

EXAMPLE 22

Preparation of emulsifiable concentrate

Compound No. 18 (40 parts), xylene (40 parts) and polyoxyethylene alkylarylether (20 parts) are homogeneously mixed together to give a emulsifiable concentrate containing 40% of the active compound. This may be diluted with water upon use and applied at a rate of 5–1000 g of the active compound per 10 ares.

EXAMPLE 23

Preparation of granules

Compound No. 6 (3 parts), calcium lignosulfonate (1 part), bentonite (30 parts) and clay (66 parts) are ground and mixed together homogeneously and the ground mixture is granulated with the addition of water. The granules so formed are dried and sieved to collect granules containing 3% of the active compound and having the desired particle size. These granules may be applied as they are at a rate of 5–1000 g of the active compound per 10 ares.

EXAMPLE 24

Preparation of granules

Compound No. 11 (3 parts), calcium lignosulfonate (1 part), bentonite (30 parts) and clay (66 parts) are ground and mixed together homogeneously and the ground mixture is granulated with the addition of water. The granules so formed are dried and sieved to collect granules containing 3% of the active compound and having the desired particle size. These granules may be applied as they are at a rate of 5–1000 g of the active compound per 10 ares.

EXAMPLE 25

Preparation of granules

Compound No. 17 (3 parts), calcium lignosulfonate (1 part), bentonite (30 parts) and clay (66 parts) are ground and mixed together homogeneously and the ground mixture is granulated with the addition of water. The granules so formed are dried and sieved to collect granules containing 3% of the active compound and having the desired particle size. These granules may be applied as they are at a rate of 5–1000 g of the active compound per 10 ares.

EXAMPLE 26

Herbicidal test on unwanted plants in farm by pre-emergence treatment

Each of biscuit pots having a top surface area of 1/2,000 ares was packed with a farm soil (alluvial soil). There were sown on the surface layer of the soil seeds each of crabgrass [*Digitaria adscendens*] (20 seeds), barnyard grass [*Echinochloa crus-galli*] (30 seeds), water foxtail [*Alopecurus aequalis*] (20 seeds), annual bluegrass [*Poa annua*] (20 seeds), green foxtail [*Setaria viridis*] (20 seeds), common purslane [*Portulaca oleracea*] (30 seeds) and common lambsquarters [*Chenopodium album*] (30 seeds) by uniformly mixing the seeds with the surface layer (about 1 cm thick) of the soil packed in each pot and the soil surface was lightly pressed down.

Just after the sowing, the soil surface of each pot was sprayed with a composition under test which was prepared by diluting with water such emulsifiable concentrate as formulated according to Example 20 in an amount of 100 l per 10 ares to give the application rates of the active compound under test as shown in Table 2 below. The test was conducted with three replicates. Twenty-one days after the spraying, the herbicidal activity of each compound under test was assessed by the following grading:

| | | |
|---|---|---|
| 5 | herbicidal activity is very high | (95% or higher) |
| 4 | herbicidal activity is high | (80~ less than 95%) |
| 3 | herbicidal activity is medium | (60~ less than 80%) |
| 2 | herbicidal activity is low | (40~ less than 60%) |
| 1 | herbicidal activity is very low | (20~ less than 40%) |
| 0 | herbicidal activity is substantially null | (less than 20%) |

The results are shown in Table 2 below.

TABLE 2

| Compound No. | Rate of active compound applied (g/10 ares) | Crab-grass | Barnyard grass | Water foxtail | Annual bluegrass | Green foxtail | Common purslane | Common lambs-quarters |
|---|---|---|---|---|---|---|---|---|
| 1 | 100 | 5 | 5 | 5 | 5 | 5 | 5 | 4 |
|   | 50 | 5 | 5 | 5 | 5 | 5 | 2 | 2 |
|   | 25 | 5 | 5 | 5 | 5 | 5 | 0 | 0 |
|   | 12.5 | 5 | 5 | 5 | 4 | 5 | 0 | 0 |
| 2 | 100 | 5 | 5 | 5 | 5 | 5 | 5 | 5 |
|   | 50 | 5 | 5 | 5 | 5 | 5 | 4 | 3 |
|   | 25 | 5 | 5 | 5 | 5 | 5 | 2 | 2 |
|   | 12.5 | 5 | 5 | 5 | 5 | 5 | 0 | 0 |
| 3 | 100 | 5 | 5 | 5 | 5 | 5 | 4 | 4 |
|   | 50 | 5 | 5 | 5 | 5 | 5 | 2 | 2 |
|   | 25 | 5 | 5 | 5 | 5 | 5 | 0 | 0 |

TABLE 2-continued

| Compound No. | Rate of active compound applied (g/10 ares) | Crab-grass | Barnyard grass | Water foxtail | Annual bluegrass | Green foxtail | Common purslane | Common lambs-quarters |
|---|---|---|---|---|---|---|---|---|
| | 12.5 | 4 | 4 | 5 | 4 | 5 | 0 | 0 |
| 4 | 100 | 5 | 5 | 5 | 5 | 5 | 4 | 4 |
| | 50 | 5 | 5 | 5 | 5 | 5 | 2 | 1 |
| | 25 | 5 | 5 | 5 | 5 | 5 | 0 | 0 |
| | 12.5 | 5 | 4 | 5 | 4 | 4 | 0 | 0 |
| 5 | 100 | 5 | 5 | 5 | 5 | 5 | 5 | 5 |
| | 50 | 5 | 5 | 5 | 5 | 5 | 4 | 3 |
| | 25 | 5 | 4 | 5 | 5 | 5 | 2 | 1 |
| | 12.5 | 4 | 4 | 5 | 4 | 4 | 0 | 0 |
| 6 | 100 | 5 | 5 | 5 | 5 | 5 | 5 | 5 |
| | 50 | 5 | 5 | 5 | 5 | 5 | 5 | 4 |
| | 25 | 5 | 5 | 5 | 5 | 5 | 3 | 2 |
| | 12.5 | 5 | 5 | 5 | 5 | 5 | 1 | 0 |
| 7 | 100 | 5 | 5 | 5 | 5 | 5 | 4 | 4 |
| | 50 | 5 | 5 | 5 | 5 | 5 | 2 | 2 |
| | 25 | 5 | 5 | 5 | 5 | 5 | 0 | 1 |
| | 12.5 | 5 | 4 | 5 | 4 | 4 | 0 | 0 |
| 8 | 100 | 5 | 5 | 5 | 5 | 5 | 4 | 4 |
| | 50 | 5 | 5 | 5 | 5 | 5 | 3 | 2 |
| | 25 | 5 | 5 | 5 | 5 | 5 | 0 | 0 |
| | 12.5 | 4 | 4 | 5 | 4 | 5 | 0 | 0 |
| 9 | 100 | 5 | 5 | 5 | 5 | 5 | 1 | 1 |
| | 50 | 5 | 5 | 5 | 4 | 5 | 0 | 0 |
| | 25 | 5 | 5 | 4 | 4 | 4 | 0 | 0 |
| | 12.5 | 4 | 4 | 3 | 3 | 3 | 0 | 0 |
| 10 | 100 | 5 | 5 | 5 | 5 | 5 | 0 | 1 |
| | 50 | 5 | 5 | 4 | 5 | 5 | 0 | 0 |
| | 25 | 4 | 4 | 4 | 4 | 4 | 0 | 0 |
| | 12.5 | 3 | 3 | 3 | 3 | 3 | 0 | 0 |
| 11 | 100 | 5 | 5 | 5 | 5 | 5 | 2 | 2 |
| | 50 | 5 | 5 | 5 | 5 | 5 | 1 | 0 |
| | 25 | 5 | 5 | 4 | 4 | 4 | 0 | 0 |
| | 12.5 | 4 | 4 | 3 | 4 | 4 | 0 | 0 |
| 12 | 100 | 5 | 5 | 5 | 5 | 5 | 3 | 3 |
| | 50 | 5 | 5 | 5 | 5 | 5 | 1 | 0 |
| | 25 | 5 | 5 | 5 | 4 | 5 | 0 | 0 |
| | 12.5 | 5 | 5 | 4 | 4 | 4 | 0 | 0 |
| 13 | 100 | 5 | 5 | 5 | 5 | 5 | 1 | 1 |
| | 50 | 5 | 5 | 4 | 5 | 4 | 0 | 0 |
| | 25 | 5 | 4 | 4 | 4 | 4 | 0 | 0 |
| | 12.5 | 4 | 4 | 3 | 3 | 3 | 0 | 0 |
| 14 | 100 | 5 | 5 | 5 | 5 | 5 | 4 | 3 |
| | 50 | 5 | 5 | 5 | 5 | 5 | 2 | 1 |
| | 25 | 5 | 5 | 5 | 5 | 5 | 1 | 0 |
| | 12.5 | 5 | 5 | 5 | 4 | 4 | 0 | 0 |
| 15 | 100 | 5 | 5 | 5 | 5 | 5 | 5 | 5 |
| | 50 | 5 | 5 | 5 | 5 | 5 | 4 | 3 |
| | 25 | 5 | 5 | 5 | 5 | 5 | 2 | 1 |
| | 12.5 | 5 | 5 | 5 | 5 | 5 | 1 | 0 |
| 16 | 100 | 5 | 5 | 5 | 5 | 5 | 3 | 3 |
| | 50 | 5 | 5 | 5 | 5 | 5 | 1 | 1 |
| | 25 | 5 | 5 | 5 | 4 | 4 | 0 | 0 |
| | 12.5 | 4 | 4 | 5 | 4 | 4 | 0 | 0 |
| 17 | 100 | 5 | 5 | 5 | 5 | 5 | 4 | 4 |
| | 50 | 5 | 5 | 5 | 5 | 5 | 3 | 2 |
| | 25 | 5 | 5 | 5 | 5 | 5 | 1 | 0 |
| | 12.5 | 4 | 5 | 4 | 4 | 4 | 0 | 0 |
| 18 | 100 | 5 | 5 | 5 | 5 | 5 | 3 | 3 |
| | 50 | 5 | 5 | 5 | 5 | 5 | 0 | 2 |
| | 25 | 5 | 5 | 4 | 5 | 4 | 0 | 0 |
| | 12.5 | 4 | 4 | 4 | 4 | 4 | 0 | 0 |
| Reference A | 100 | 5 | 4 | 4 | 4 | 5 | 3 | 3 |
| | 50 | 4 | 3 | 4 | 3 | 4 | 1 | 1 |
| | 25 | 4 | 2 | 2 | 2 | 3 | 0 | 0 |
| | 12.5 | 3 | 2 | 2 | 2 | 2 | 0 | 0 |
| B | 100 | 5 | 4 | 4 | 4 | 4 | 2 | 1 |
| | 50 | 4 | 2 | 4 | 2 | 4 | 0 | 0 |
| | 25 | 3 | 1 | 2 | 1 | 2 | 0 | 0 |
| | 12.5 | 1 | 0 | 0 | 0 | 1 | 0 | 0 |
| C | 100 | 4 | 3 | 4 | 3 | 4 | 0 | 2 |
| | 50 | 2 | 1 | 2 | 2 | 2 | 0 | 0 |
| | 25 | 1 | 0 | 1 | 0 | 1 | 0 | 0 |
| | 12.5 | 0 | 0 | 0 | 0 | 0 | 0 | 0 |
| D | 100 | 5 | 5 | 4 | 4 | 4 | 4 | 2 |
| | 50 | 3 | 3 | 3 | 2 | 3 | 2 | 0 |
| | 25 | 1 | 1 | 1 | 1 | 1 | 0 | 0 |
| | 12.5 | 0 | 0 | 0 | 0 | 0 | 0 | 0 |

TABLE 2-continued

| Compound No. | Rate of active compound applied (g/10 ares) | Crab-grass | Barnyard grass | Water foxtail | Annual bluegrass | Green foxtail | Common purslane | Common lambs-quarters |
|---|---|---|---|---|---|---|---|---|
| E | 100 | 4 | 3 | 4 | 3 | 3 | 3 | 0 |
|   | 50 | 4 | 2 | 3 | 3 | 1 | 2 | 0 |
|   | 25 | 2 | 0 | 1 | 1 | 0 | 1 | 0 |
|   | 12.5 | 0 | 0 | 0 | 0 | 0 | 0 | 0 |
| F | 100 | 4 | 4 | 4 | 4 | 4 | 0 | 0 |
|   | 50 | 3 | 4 | 4 | 3 | 3 | 0 | 0 |
|   | 25 | 3 | 3 | 2 | 3 | 3 | 0 | 0 |
|   | 12.5 | 2 | 1 | 2 | 1 | 1 | 0 | 0 |
| G | 100 | 4 | 4 | 4 | 4 | 3 | 0 | 0 |
|   | 50 | 3 | 4 | 3 | 3 | 3 | 0 | 0 |
|   | 25 | 2 | 2 | 3 | 2 | 1 | 0 | 0 |
|   | 12.5 | 0 | 0 | 1 | 0 | 0 | 1 | 0 |
| H | 100 | 4 | 5 | 4 | 4 | 4 | 0 | 0 |
|   | 50 | 4 | 3 | 3 | 4 | 2 | 0 | 0 |
|   | 25 | 3 | 2 | 2 | 3 | 2 | 0 | 0 |
|   | 12.5 | 1 | 1 | 2 | 1 | 1 | 0 | 0 |
| I | 100 | 3 | 4 | 3 | 3 | 4 | 0 | 0 |
|   | 50 | 2 | 2 | 3 | 2 | 1 | 0 | 0 |
|   | 25 | 2 | 1 | 1 | 1 | 1 | 0 | 0 |
|   | 12.5 | 1 | 0 | 0 | 0 | 0 | 0 | 0 |
| J | 100 | 4 | 4 | 4 | 4 | 4 | 1 | 1 |
|   | 50 | 4 | 3 | 4 | 3 | 4 | 0 | 0 |
|   | 25 | 2 | 0 | 2 | 1 | 1 | 0 | 0 |
|   | 12.5 | 1 | 0 | 2 | 0 | 0 | 0 | 0 |
| K | 100 | 4 | 4 | 4 | 4 | 4 | 2 | 2 |
|   | 50 | 3 | 2 | 3 | 3 | 3 | 0 | 0 |
|   | 25 | 2 | 1 | 1 | 2 | 1 | 0 | 0 |
|   | 12.5 | 1 | 0 | 1 | 0 | 0 | 0 | 0 |
| L | 100 | 4 | 4 | 4 | 4 | 4 | 2 | 2 |
|   | 50 | 4 | 2 | 3 | 2 | 4 | 0 | 1 |
|   | 25 | 3 | 1 | 2 | 1 | 2 | 0 | 0 |
|   | 12.5 | 1 | 0 | 1 | 0 | 1 | 0 | 0 |
| M | 100 | 4 | 4 | 4 | 3 | 4 | 1 | 2 |
|   | 50 | 3 | 2 | 2 | 3 | 3 | 0 | 1 |
|   | 25 | 1 | 1 | 1 | 1 | 1 | 0 | 0 |
|   | 12.5 | 0 | 0 | 0 | 0 | 0 | 0 | 0 |

The references A to M used as above for the purpose of comparison are identified as follows:

Reference A:

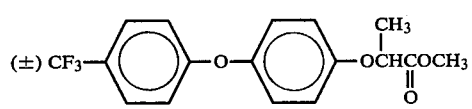

(Japanese Patent Application KOKAI Sho 52-83618)

Reference B:

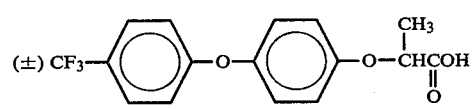

(Japanese Patent Application KOKAI Sho 52-83618)

Reference C:

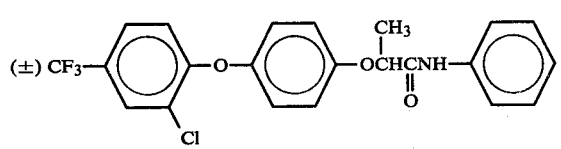

(Japanese Patent Applicaton KOKAI Sho 52-83618)

Reference D: Alachlor [A commercial product; 2-chloro-2',6'-diethyl-N-(methoxymethyl)acetanilide]

Reference E: Trifluralin [A commercial product; α,α,α-trifluoro-2,6-dinitro-N,N-dipropyl-para-toluidine]

Reference F:

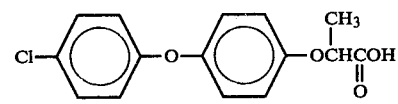

(Japanese Patent Publication No. 8727/79)

Reference G:

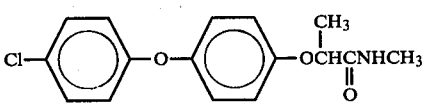

(Japanese Patent Publication No. 8727/79)

Reference H:

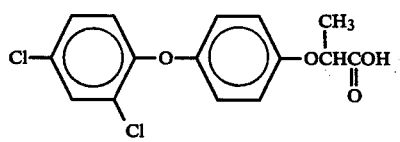

(Japanese Patent Publication No. 8727/79)
Reference I:

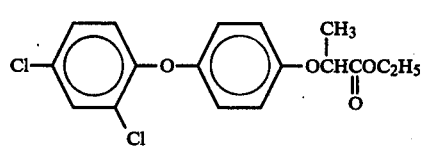

(Japanese Patent Publication No. 8727/79)
Reference J:

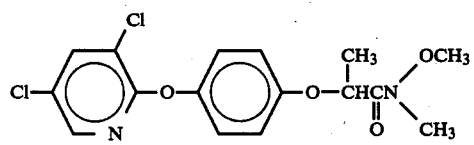

(Japanese Patent Application KOKAI Sho 52-125626)
Reference K:

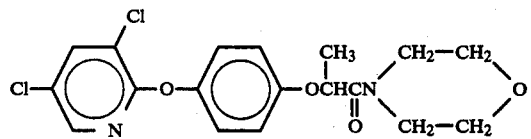

(Japanese Patent Application KOKAI Sho 52-125626)
Reference L:

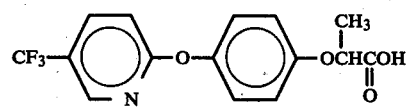

(Japanese Patent Application KOKAI Sho 54-122728)
Reference M:

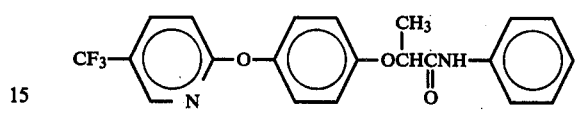

(Japanese Patent Applicaton KOKAI Sho 54-122728)

EXAMPLE 27

Phytotoxic test on farm crop plants by pre-emergence treatment

Each of biscuit pots having a top surface area of 1/10,000 ares was packed with a farm soil (alluvial farm). There were sown on the surface of the soil seeds each of soya bean (5 seeds), small red bean (5 seeds), sugar beet (10 seeds), radish (15 seeds), tomato (5 seeds) and wheat (10 seeds). Then, the surface was covered with the same soil in 1 cm thickness and lightly pressed down.

Just after the seeding, the soil surface of each pot was sprayed with a composition under test which was prepared by diluting with water such emulsifiable concentrate as formulated in Example 20 in an amount of 100 l per 10 ares to give the application rates of the active compound under test as shown in Table 3 below. The test was conducted with three replicates. Twenty-one days after the spraying, the degree of phytotoxicity on each of the crop plants under test was assessed by the following grading:

5: Phytotoxicity is very high
4: Phytotoxicity is high
3: Phytotoxicity is medium
2: Phytotoxicity is low
1: Phytotoxicity is very low
0: Phytotoxicity is not observed The results are shown in Table 3 below.

TABLE 3

| Compound No. | Rate of active compound applied (g/10 ares) | Soya bean | Small red bean | Sugar beet | Radish | Tomato | Wheat |
|---|---|---|---|---|---|---|---|
| 1 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| 2 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| 3 | 400 | 0 | 1 | 0 | 0 | 0 | 5 |
|   | 200 | 0 | 0 | 0 | 0 | 0 | 5 |
|   | 100 | 0 | 0 | 0 | 0 | 0 | 4 |
| 4 | 400 | 0 | 1 | 0 | 0 | 0 | 5 |
|   | 200 | 0 | 0 | 0 | 0 | 0 | 5 |
|   | 100 | 0 | 0 | 0 | 0 | 0 | 4 |
| 5 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| 6 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |

TABLE 3-continued

| Compound No. | Rate of active compound applied (g/10 ares) | Soya bean | Small red bean | Sugar beet | Radish | Tomato | Wheat |
|---|---|---|---|---|---|---|---|
| 7 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| 8 | 400 | 0 | 1 | 0 | 0 | 0 | 5 |
|   | 200 | 0 | 0 | 0 | 0 | 0 | 5 |
|   | 100 | 0 | 0 | 0 | 0 | 0 | 5 |
| 9 | 400 | 0 | 0 | 0 | 0 | 0 | 5 |
|   | 200 | 0 | 0 | 0 | 0 | 0 | 5 |
|   | 100 | 0 | 0 | 0 | 1 | 1 | 5 |
| 10 | 400 | 0 | 0 | 0 | 0 | 0 | 5 |
|   | 200 | 0 | 0 | 0 | 0 | 0 | 5 |
|   | 100 | 0 | 0 | 0 | 0 | 1 | 4 |
| 11 | 400 | 0 | 0 | 0 | 0 | 0 | 5 |
|   | 200 | 0 | 0 | 0 | 0 | 0 | 5 |
|   | 100 | 0 | 0 | 0 | 0 | 1 | 5 |
| 12 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| 13 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 4 |
| 14 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| 15 | 400 | 0 | 0 | 0 | 0 | 1 | 5 |
|   | 200 | 0 | 0 | 0 | 0 | 0 | 5 |
|   | 100 | 0 | 0 | 0 | 0 | 0 | 5 |
| 16 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| 17 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| 18 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| Reference A | 400 | 3 | 4 | 2 | 3 | 4 | 5 |
|   | 200 | 2 | 3 | 1 | 2 | 2 | 5 |
|   | 100 | 0 | 1 | 0 | 0 | 1 | 4 |
| B | 400 | 3 | 3 | 2 | 3 | 4 | 5 |
|   | 200 | 1 | 2 | 1 | 2 | 1 | 5 |
|   | 100 | 0 | 1 | 0 | 1 | 0 | 4 |
| C | 400 | 4 | 3 | 2 | 3 | 3 | 5 |
|   | 200 | 2 | 0 | 1 | 1 | 2 | 5 |
|   | 100 | 0 | 0 | 0 | 0 | 1 | 3 |
| D | 400 | 2 | 5 | 5 | 2 | 5 | 5 |
|   | 200 | 1 | 4 | 4 | 1 | 3 | 4 |
|   | 100 | 0 | 3 | 2 | 0 | 2 | 3 |
| E | 400 | 1 | 4 | 5 | 2 | 3 | 5 |
|   | 200 | 0 | 2 | 3 | 1 | 2 | 4 |
|   | 100 | 0 | 1 | 2 | 0 | 1 | 3 |
| F | 400 | 2 | 3 | 2 | 2 | 2 | 5 |
|   | 200 | 1 | 2 | 1 | 2 | 1 | 5 |
|   | 100 | 0 | 1 | 0 | 0 | 1 | 5 |
| G | 400 | 1 | 2 | 2 | 2 | 1 | 5 |
|   | 200 | 1 | 1 | 1 | 1 | 0 | 4 |
|   | 100 | 0 | 0 | 0 | 0 | 0 | 4 |
| H | 400 | 3 | 3 | 3 | 3 | 2 | 5 |
|   | 200 | 1 | 2 | 1 | 2 | 1 | 5 |
|   | 100 | 1 | 1 | 1 | 1 | 1 | 5 |
| I | 400 | 3 | 3 | 3 | 3 | 3 | 5 |
|   | 200 | 1 | 2 | 2 | 2 | 2 | 5 |
|   | 100 | 1 | 1 | 1 | 2 | 1 | 5 |
| J | 400 | 3 | 2 | 2 | 3 | 1 | 5 |
|   | 200 | 2 | 1 | 1 | 2 | 0 | 5 |
|   | 100 | 0 | 0 | 0 | 1 | 0 | 4 |
| K | 400 | 2 | 2 | 2 | 3 | 2 | 5 |
|   | 200 | 1 | 1 | 1 | 2 | 1 | 5 |
|   | 100 | 1 | 1 | 1 | 1 | 1 | 3 |
| L | 400 | 3 | 3 | 2 | 2 | 2 | 5 |
|   | 200 | 2 | 2 | 1 | 1 | 1 | 5 |
|   | 100 | 1 | 0 | 1 | 0 | 0 | 4 |
| M | 400 | 2 | 2 | 2 | 2 | 2 | 5 |
|   | 200 | 1 | 1 | 1 | 1 | 2 | 4 |
|   | 100 | 1 | 1 | 1 | 1 | 1 | 4 |

EXAMPLE 28

Herbicidal test on unwanted plants in farm by post-emergence treatment

Each of biscuit pots having a top surface area of 1/10,000 ares was packed with a farm soil (alluvial soil). There were sown on the surface of the soil seeds each of crabgrass (30 seeds), barnyard grass (50 seeds), water foxtail (40 seeds), annual bluegrass (40 seeds), green foxtail (40 seeds), common purslane (50 seeds) and common lambsquarters (40 seeds). Then, the surface was covered with the same soil in 1 cm thickness and lightly pressed down.

In each of the pots, the crabgrass (4 leaved stage), barnyard grass (3 leaved stage), water foxtail (4 leaved stage), annual bluegrass (3 to 4 leaved stage), green foxtail (4 leaved stage), common purslane (2 leaved stage) and common lambsquarters (2 leaved stage) were grown to such degrees as shown in the above parentheses, respectively. These seedlings each were sprayed, at the respective growing stages, with a composition under test which was prepared by diluting with water such emulsifiable concentrate as formulated according to Example 20 in an amount of 100 l per 10 ares to give the application rates of the active compound under test as shown in Table 4 below. The test was conducted with three replicates. Twenty-one days after the spraying, the damage to plants, that is the harbicidal activity of each compound under test, was assessed by the same grading used in Example 26. The results are shown in Table 4 below.

TABLE 4

| Compound No. | Rate of active compound applied (g/10 ares) | Crab-grass | Barnyard grass | Water foxtail | Annual bluegrass | Green foxtail | Common purslane | Common lambs-quarters |
|---|---|---|---|---|---|---|---|---|
| 1 | 200 | 5 | 5 | 5 | 5 | 5 | 5 | 4 |
|   | 100 | 5 | 5 | 5 | 5 | 5 | 3 | 2 |
|   | 50  | 5 | 5 | 5 | 5 | 5 | 1 | 0 |
|   | 25  | 5 | 4 | 4 | 5 | 5 | 0 | 0 |
| 2 | 200 | 5 | 5 | 5 | 5 | 5 | 5 | 4 |
|   | 100 | 5 | 5 | 5 | 5 | 5 | 4 | 2 |
|   | 50  | 5 | 5 | 5 | 5 | 5 | 2 | 1 |
|   | 25  | 5 | 5 | 5 | 4 | 5 | 0 | 0 |
| 3 | 200 | 5 | 5 | 5 | 5 | 5 | 5 | 3 |
|   | 100 | 5 | 5 | 5 | 5 | 5 | 3 | 1 |
|   | 50  | 5 | 5 | 4 | 5 | 5 | 1 | 0 |
|   | 25  | 5 | 4 | 4 | 4 | 4 | 0 | 0 |
| 4 | 200 | 5 | 5 | 5 | 5 | 5 | 4 | 3 |
|   | 100 | 5 | 5 | 5 | 5 | 5 | 2 | 2 |
|   | 50  | 5 | 5 | 5 | 5 | 5 | 0 | 0 |
|   | 25  | 4 | 4 | 4 | 4 | 5 | 0 | 0 |
| 5 | 200 | 5 | 5 | 5 | 5 | 5 | 5 | 4 |
|   | 100 | 5 | 5 | 5 | 5 | 5 | 3 | 2 |
|   | 50  | 5 | 5 | 5 | 4 | 5 | 1 | 0 |
|   | 25  | 5 | 4 | 5 | 4 | 5 | 0 | 0 |
| 6 | 200 | 5 | 5 | 5 | 5 | 5 | 5 | 5 |
|   | 100 | 5 | 5 | 5 | 5 | 5 | 4 | 4 |
|   | 50  | 5 | 5 | 5 | 5 | 5 | 2 | 2 |
|   | 25  | 5 | 5 | 5 | 5 | 5 | 2 | 0 |
| 7 | 200 | 5 | 5 | 5 | 5 | 5 | 4 | 3 |
|   | 100 | 5 | 5 | 5 | 5 | 5 | 2 | 2 |
|   | 50  | 5 | 5 | 5 | 5 | 5 | 0 | 0 |
|   | 25  | 4 | 5 | 4 | 5 | 4 | 0 | 0 |
| 8 | 200 | 5 | 5 | 5 | 5 | 5 | 4 | 3 |
|   | 100 | 5 | 5 | 5 | 5 | 5 | 2 | 1 |
|   | 50  | 5 | 5 | 4 | 5 | 5 | 0 | 0 |
|   | 25  | 5 | 4 | 4 | 5 | 4 | 0 | 0 |
| 9 | 200 | 5 | 5 | 5 | 5 | 5 | 1 | 1 |
|   | 100 | 5 | 5 | 5 | 5 | 5 | 0 | 0 |
|   | 50  | 5 | 5 | 5 | 5 | 5 | 0 | 0 |
|   | 25  | 4 | 4 | 4 | 4 | 4 | 0 | 0 |
| 10 | 200 | 5 | 5 | 5 | 5 | 5 | 2 | 1 |
|    | 100 | 5 | 5 | 5 | 5 | 5 | 1 | 0 |
|    | 50  | 4 | 5 | 4 | 4 | 5 | 0 | 0 |
|    | 25  | 4 | 4 | 4 | 4 | 4 | 0 | 0 |
| 11 | 200 | 5 | 5 | 5 | 5 | 5 | 1 | 2 |
|    | 100 | 5 | 5 | 5 | 5 | 5 | 1 | 1 |
|    | 50  | 5 | 5 | 5 | 5 | 5 | 0 | 0 |
|    | 25  | 4 | 5 | 4 | 5 | 4 | 0 | 0 |
| 12 | 200 | 5 | 5 | 5 | 5 | 5 | 2 | 2 |
|    | 100 | 5 | 5 | 5 | 5 | 5 | 1 | 1 |
|    | 50  | 5 | 5 | 5 | 5 | 5 | 0 | 1 |
|    | 25  | 5 | 5 | 5 | 5 | 4 | 0 | 0 |
| 13 | 200 | 5 | 5 | 5 | 5 | 5 | 1 | 2 |
|    | 100 | 5 | 5 | 5 | 5 | 5 | 0 | 1 |
|    | 50  | 4 | 5 | 5 | 5 | 5 | 0 | 0 |
|    | 25  | 4 | 4 | 4 | 5 | 4 | 0 | 0 |
| 14 | 200 | 5 | 5 | 5 | 5 | 5 | 4 | 3 |
|    | 100 | 5 | 5 | 5 | 5 | 5 | 3 | 2 |
|    | 50  | 5 | 5 | 5 | 5 | 5 | 1 | 1 |
|    | 25  | 5 | 4 | 4 | 4 | 5 | 0 | 0 |
| 15 | 200 | 5 | 5 | 5 | 5 | 5 | 5 | 4 |

TABLE 4-continued

| Compound No. | Rate of active compound applied (g/10 ares) | Crab-grass | Barnyard grass | Water foxtail | Annual bluegrass | Green foxtail | Common purslane | Common lambs-quarters |
|---|---|---|---|---|---|---|---|---|
| | 100 | 5 | 5 | 5 | 5 | 5 | 4 | 3 |
| | 50 | 5 | 5 | 5 | 5 | 5 | 2 | 1 |
| | 25 | 5 | 5 | 5 | 5 | 5 | 1 | 0 |
| 16 | 200 | 5 | 5 | 5 | 5 | 5 | 4 | 2 |
| | 100 | 5 | 5 | 5 | 5 | 5 | 2 | 1 |
| | 50 | 5 | 4 | 4 | 5 | 5 | 0 | 0 |
| | 25 | 5 | 4 | 4 | 4 | 4 | 0 | 0 |
| 17 | 200 | 5 | 5 | 5 | 5 | 5 | 4 | 3 |
| | 100 | 5 | 5 | 5 | 5 | 5 | 2 | 1 |
| | 50 | 5 | 5 | 4 | 5 | 5 | 0 | 0 |
| | 25 | 5 | 5 | 4 | 4 | 4 | 0 | 0 |
| 18 | 200 | 5 | 5 | 5 | 5 | 5 | 3 | 2 |
| | 100 | 5 | 5 | 5 | 5 | 5 | 1 | 0 |
| | 50 | 5 | 5 | 4 | 4 | 5 | 0 | 0 |
| | 25 | 4 | 5 | 4 | 4 | 4 | 0 | 0 |
| Reference A | 200 | 5 | 5 | 5 | 4 | 5 | 3 | 2 |
| | 100 | 5 | 4 | 5 | 4 | 4 | 1 | 1 |
| | 50 | 3 | 2 | 4 | 2 | 3 | 0 | 0 |
| | 25 | 2 | 1 | 2 | 1 | 2 | 0 | 0 |
| Reference B | 200 | 4 | 4 | 5 | 3 | 4 | 2 | 0 |
| | 100 | 4 | 3 | 4 | 3 | 3 | 0 | 0 |
| | 50 | 2 | 1 | 3 | 1 | 3 | 0 | 0 |
| | 25 | 1 | 0 | 1 | 0 | 1 | 0 | 0 |
| Reference C | 200 | 4 | 4 | 4 | 4 | 4 | 3 | 1 |
| | 100 | 4 | 3 | 4 | 3 | 4 | 0 | 0 |
| | 50 | 3 | 2 | 3 | 2 | 3 | 0 | 0 |
| | 25 | 1 | 1 | 2 | 0 | 1 | 0 | 0 |
| Reference F | 200 | 4 | 4 | 4 | 4 | 4 | 1 | 0 |
| | 100 | 4 | 3 | 4 | 3 | 4 | 0 | 0 |
| | 50 | 3 | 3 | 3 | 2 | 3 | 0 | 0 |
| | 25 | 3 | 2 | 2 | 2 | 2 | 0 | 0 |
| Reference G | 200 | 4 | 4 | 4 | 4 | 4 | 1 | 0 |
| | 100 | 3 | 2 | 3 | 4 | 3 | 0 | 0 |
| | 50 | 3 | 1 | 1 | 2 | 3 | 0 | 0 |
| | 25 | 2 | 0 | 0 | 1 | 1 | 0 | 0 |
| Reference H | 200 | 4 | 4 | 4 | 4 | 4 | 1 | 1 |
| | 100 | 4 | 3 | 3 | 4 | 3 | 0 | 0 |
| | 50 | 3 | 3 | 2 | 3 | 3 | 0 | 0 |
| | 25 | 2 | 1 | 1 | 1 | 2 | 0 | 0 |
| Reference I | 200 | 4 | 4 | 4 | 4 | 4 | 2 | 1 |
| | 100 | 4 | 4 | 3 | 4 | 4 | 1 | 0 |
| | 50 | 3 | 3 | 3 | 3 | 3 | 0 | 0 |
| | 25 | 2 | 2 | 1 | 2 | 3 | 0 | 0 |
| Reference J | 200 | 4 | 4 | 4 | 4 | 4 | 2 | 1 |
| | 100 | 4 | 3 | 4 | 3 | 3 | 1 | 0 |
| | 50 | 3 | 2 | 3 | 1 | 2 | 0 | 0 |
| | 25 | 1 | 0 | 2 | 0 | 1 | 0 | 0 |
| Reference K | 200 | 4 | 3 | 4 | 3 | 4 | 1 | 1 |
| | 100 | 3 | 2 | 3 | 3 | 2 | 0 | 0 |
| | 50 | 2 | 1 | 2 | 2 | 0 | 0 | 0 |
| | 25 | 1 | 0 | 1 | 0 | 0 | 0 | 0 |
| Reference L | 200 | 4 | 4 | 4 | 4 | 4 | 2 | 2 |
| | 100 | 4 | 3 | 3 | 3 | 4 | 1 | 0 |
| | 50 | 2 | 1 | 2 | 1 | 3 | 0 | 0 |
| | 25 | 1 | 0 | 1 | 1 | 1 | 0 | 0 |
| Reference M | 200 | 4 | 4 | 4 | 4 | 4 | 1 | 1 |
| | 100 | 3 | 2 | 3 | 2 | 3 | 0 | 0 |
| | 50 | 2 | 1 | 1 | 1 | 2 | 0 | 0 |
| | 25 | 0 | 0 | 0 | 0 | 0 | 0 | 0 |
| Reference N | 200 | 5 | 4 | 5 | 4 | 4 | 1 | 1 |
| | 100 | 4 | 4 | 3 | 3 | 4 | 0 | 0 |
| | 50 | 2 | 2 | 3 | 1 | 2 | 0 | 0 |
| | 25 | 1 | 0 | 1 | 0 | 0 | 0 | 0 |

The reference N used above for the purpose of comparison is identified as follows:

Reference N: Alloxydim-sodium [A commercial product; methyl 3-[1-(allyloxyimino)butylidene]-6,6-dimethyl-2,4-dioxocyclohexane carboxylate sodium salt]

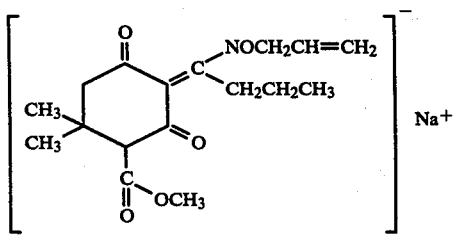

EXAMPLE 29

Phytotoxic test on farm crop plants by post-emergence treatment

Each of biscuit pots having a top surface area of 1/10,000 ares was packed with a farm soil (alluvial soil). There were sown on the surface of the soil seeds each of soya bean (5 seeds), small red bean (5 seeds), sugar beet (10 seeds), radish (10 seeds), tomato (5 seeds), and wheat (10 seeds). Then, the surface was covered with the same soil in 1 cm thickness and lightly pressed thereon.

When each of the test plants sown was grown to 3-4 leaved stage, the stalks and leaves of the growing plants were sprayed with a composition under test which was prepared by diluting with water such emulsifiable concentrate as formulated in Example 20 in an amount of 100 l per 10 ares to give the application rates of the active compound under test as shown in Table 5 below. The test was conducted with three replicates. Twenty-one days after the spraying, the degree of phytotoxicity on each of the crop plants under test was assessed by the same grading used in Example 27. The results are shown in Table 5 below.

TABLE 5

| Compound No. | Rate of active compound applied (g/10 ares) | Soya bean | Small red bean | Sugar beet | Radish | Tomato | Wheat |
|---|---|---|---|---|---|---|---|
| 1 | 400 | 0 | 1 | 0 | 0 | 1 | 5 |
|   | 200 | 0 | 0 | 0 | 0 | 0 | 5 |
|   | 100 | 0 | 0 | 0 | 0 | 0 | 5 |
| 2 | 400 | 0 | 1 | 0 | 1 | 1 | 5 |
|   | 200 | 0 | 0 | 0 | 0 | 0 | 5 |
|   | 100 | 0 | 0 | 0 | 0 | 0 | 5 |
| 3 | 400 | 0 | 1 | 0 | 0 | 1 | 5 |
|   | 200 | 0 | 0 | 0 | 0 | 0 | 5 |
|   | 100 | 0 | 0 | 0 | 0 | 0 | 5 |
| 4 | 400 | 0 | 0 | 0 | 0 | 1 | 5 |
|   | 200 | 0 | 0 | 0 | 0 | 0 | 5 |
|   | 100 | 0 | 0 | 0 | 0 | 0 | 5 |
| 5 | 400 | 0 | 0 | 0 | 0 | 1 | 5 |
|   | 200 | 0 | 0 | 0 | 0 | 0 | 5 |
|   | 100 | 0 | 0 | 0 | 0 | 0 | 5 |
| 6 | 400 | 0 | 1 | 0 | 0 | 1 | 5 |
|   | 200 | 0 | 0 | 0 | 0 | 0 | 5 |
|   | 100 | 0 | 0 | 0 | 0 | 0 | 5 |
| 7 | 400 | 0 | 1 | 0 | 0 | 0 | 5 |
|   | 200 | 0 | 0 | 0 | 0 | 0 | 5 |
|   | 100 | 0 | 0 | 0 | 0 | 0 | 5 |
| 8 | 400 | 0 | 1 | 0 | 0 | 1 | 5 |
|   | 200 | 0 | 0 | 0 | 0 | 0 | 5 |
|   | 100 | 0 | 0 | 0 | 0 | 0 | 5 |
| 9 | 400 | 0 | 1 | 0 | 1 | 0 | 5 |
|   | 200 | 0 | 0 | 0 | 0 | 0 | 5 |
|   | 100 | 0 | 0 | 0 | 0 | 0 | 5 |
| 10 | 400 | 0 | 0 | 0 | 1 | 1 | 5 |
|   | 200 | 0 | 0 | 0 | 0 | 0 | 5 |
|   | 100 | 0 | 0 | 0 | 0 | 0 | 4 |
| 11 | 400 | 0 | 1 | 0 | 1 | 0 | 5 |
|   | 200 | 0 | 0 | 0 | 0 | 0 | 5 |
|   | 100 | 0 | 0 | 0 | 0 | 0 | 4 |
| 12 | 400 | 0 | 1 | 0 | 1 | 1 | 5 |
|   | 200 | 0 | 0 | 0 | 0 | 0 | 5 |
|   | 100 | 0 | 0 | 0 | 0 | 0 | 5 |
| 13 | 400 | 0 | 0 | 0 | 1 | 0 | 5 |
|   | 200 | 0 | 0 | 0 | 0 | 0 | 4 |
|   | 100 | 0 | 0 | 0 | 0 | 0 | 3 |
| 14 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| 15 | 400 | 0 | 1 | 0 | 1 | 0 | 5 |
|   | 200 | 0 | 0 | 0 | 0 | 0 | 5 |
|   | 100 | 0 | 0 | 0 | 0 | 0 | 5 |
| 16 | 400 | 0 | 0 | 0 | 1 | 0 | 5 |
|   | 200 | 0 | 0 | 0 | 0 | 0 | 5 |
|   | 100 | 0 | 0 | 0 | 0 | 0 | 5 |
| 17 | 400 | 0 | 0 | 0 | 0 | 0 | 5 |
|   | 200 | 0 | 0 | 0 | 0 | 0 | 5 |
|   | 100 | 0 | 0 | 0 | 0 | 0 | 5 |
| 18 | 400 | 0 | 0 | 0 | 1 | 0 | 5 |
|   | 200 | 0 | 0 | 0 | 0 | 0 | 5 |
|   | 100 | 0 | 0 | 0 | 0 | 0 | 5 |
| Reference A | 400 | 2 | 3 | 2 | 2 | 2 | 5 |
|   | 200 | 1 | 2 | 1 | 2 | 1 | 5 |
|   | 100 | 0 | 1 | 0 | 0 | 0 | 4 |
| Reference | 400 | 2 | 2 | 2 | 2 | 1 | 5 |

TABLE 5-continued

| Compound No. | Rate of active compound applied (g/10 ares) | Soya bean | Small red bean | Sugar beet | Radish | Tomato | Wheat |
|---|---|---|---|---|---|---|---|
| B | 200 | 0 | 2 | 1 | 1 | 1 | 5 |
|  | 100 | 0 | 1 | 0 | 0 | 0 | 4 |
| Reference C | 400 | 2 | 2 | 1 | 1 | 1 | 5 |
|  | 200 | 0 | 1 | 0 | 0 | 0 | 5 |
|  | 100 | 0 | 1 | 0 | 0 | 0 | 4 |
| Reference F | 400 | 2 | 3 | 2 | 3 | 2 | 5 |
|  | 200 | 1 | 2 | 1 | 1 | 1 | 5 |
|  | 100 | 0 | 1 | 1 | 1 | 1 | 4 |
| Reference G | 400 | 2 | 2 | 2 | 2 | 2 | 5 |
|  | 200 | 1 | 1 | 1 | 1 | 1 | 3 |
|  | 100 | 0 | 1 | 0 | 0 | 0 | 3 |
| Reference H | 400 | 3 | 3 | 2 | 3 | 2 | 5 |
|  | 200 | 2 | 2 | 1 | 2 | 2 | 5 |
|  | 100 | 1 | 2 | 1 | 1 | 1 | 4 |
| Reference I | 400 | 3 | 3 | 3 | 3 | 3 | 5 |
|  | 200 | 3 | 2 | 1 | 3 | 2 | 5 |
|  | 100 | 2 | 2 | 1 | 1 | 2 | 5 |
| Reference J | 400 | 3 | 2 | 3 | 3 | 2 | 5 |
|  | 200 | 2 | 1 | 2 | 2 | 1 | 4 |
|  | 100 | 1 | 1 | 1 | 1 | 0 | 3 |
| Reference K | 400 | 3 | 2 | 2 | 2 | 2 | 5 |
|  | 200 | 2 | 1 | 1 | 2 | 1 | 4 |
|  | 100 | 1 | 0 | 0 | 1 | 0 | 3 |
| Reference L | 400 | 3 | 3 | 3 | 3 | 3 | 5 |
|  | 200 | 2 | 2 | 1 | 2 | 2 | 4 |
|  | 100 | 2 | 1 | 1 | 1 | 2 | 4 |
| Reference M | 400 | 3 | 3 | 3 | 2 | 2 | 5 |
|  | 200 | 2 | 1 | 2 | 1 | 2 | 4 |
|  | 100 | 1 | 1 | 1 | 0 | 1 | 3 |
| Reference N | 400 | 2 | 2 | 2 | 1 | 2 | 5 |
|  | 200 | 1 | 2 | 1 | 0 | 1 | 5 |
|  | 100 | 0 | 0 | 0 | 0 | 0 | 4 |

What we claim is:

1. 2-(Substituted-phenoxy)propionic acid derivative having the formula:

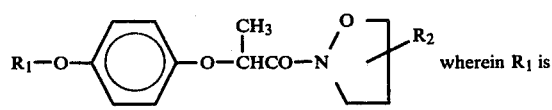

wherein $R_1$ is

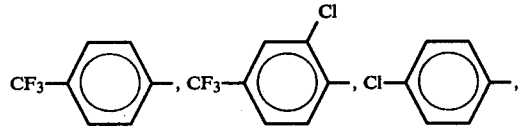

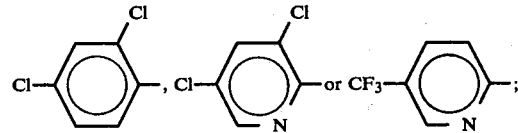

and $R_2$ is a hydrogen atom or a lower alkyl group.

2. A compound claimed in claim 1 in the form of d-isomer.

3. A compound claimed in claim 1 in the form of l-isomer.

4. A compound claimed in claim 1 in the form of racemic modification.

5. 2-(Substituted-phenoxy)propionic acid derivative having the formula:

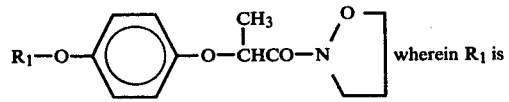

wherein $R_1$ is

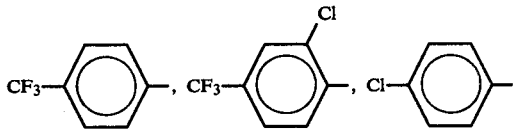

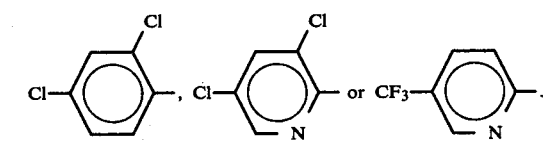

6. A compound claimed in claim 5 in the form of d-isomer.

7. A compound claimed in claim 5 in the form of l-isomer.

8. A compound claimed in claim 5 in the form of racemic modification.

9. A compound as claimed in claim 1 which is selected from:

N-[2-[4-(4-trifluoromethylphenoxy)phenoxy]propionyl]isoxazolidine;

N-[2-[4-(4-trifluoromethylphenoxy)phenoxy]propionyl]-5-methylisoxazolidine;

N-[2-[4-(4-trifluoromethylphenoxy)phenoxy]propionyl]-3-methylisoxazolidine;

N-[2-[4-(2-chloro-4-trifluoromethylphenoxy)phenoxy]propionyl]isoxazolidine;

N-[2-[4-(2-chloro-4-trifluoromethylphenoxy)phenoxy]propionyl]-5-methylisoxazolidine;

N-[2-[4-(2-chloro-4-trifluoromethylphenoxy)phenoxy]propionyl]-3-methylisoxazolidine;

N-[2-[4-(4-chlorophenoxy)phenoxy]propionyl]isoxazolidine;

N-[2-[4-(4-chlorophenoxy)phenoxy]propionyl]-5-methylisoxazolidine;

N-[2-[4-(2,4-dichlorophenoxy)phenoxy]propionyl]isoxazolidine;

N-[2-[4-(2,4-dichlorophenoxy)phenoxy]propionyl]-5-methylisoxazolidine;

N-[2-[4-(3,5-dichloro-2-pyridyloxy)phenoxy]propionyl]isoxazolidine;

N-[2-[4-(3,5-dichloro-2-pyridyloxy)phenoxy]propionyl]-5-methylisoxazolidine;

N-[2-[4-(5-trifluoromethyl-2-pyridyloxy)phenoxy]propionyl]isoxazolidine; and

N-[2-[4-(5-trifluoromethyl-2-pyridyloxy)phenoxy]propionyl]-5-methylisoxazolidine.

10. A compound claimed in claim 9 in the form of d-isomer.

11. A compound claimed in claim 9 in the form of l-isomer.

12. A compound claimed in claim 9 in the form of racemic modification.

13. A method of inhibiting the growth of unwanted plants which comprises applying to the plants or to the locus thereof an effective herbicidal amount of a 2-(substituted-phenoxy)propionic acid derivative of the formula:

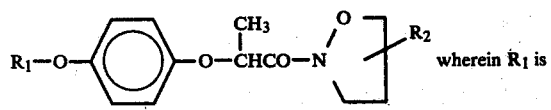 wherein $R_1$ is

-continued

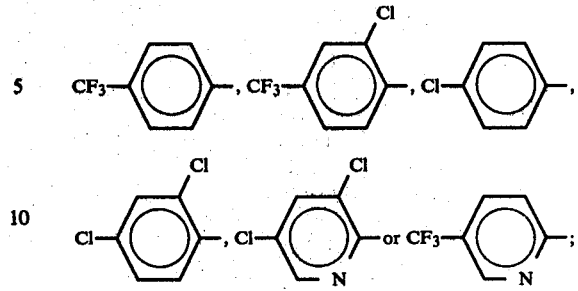

and $R_2$ is a hydrogen atom or a lower alkyl group, the compound being in the form of d-isomer, l-isomer or a mixture thereof.

14. A herbicidal composition comprising as an active ingredient a effective amount of 2-(substituted-phenoxy)propionic acid derivative of the general formula:

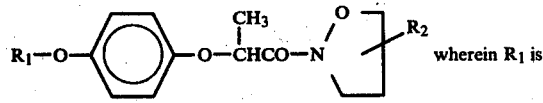 wherein $R_1$ is

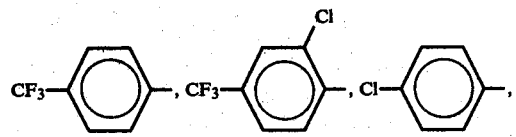

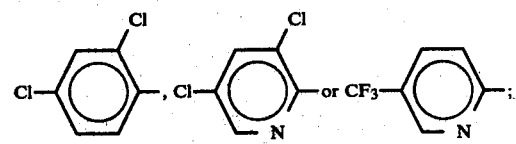

and $R_2$ is a hydrogen atom or a lower alkyl group in admixture with a solid or liquid diluent or carrier.

* * * * *